United States Patent [19]

Plummer

[11] Patent Number: 5,569,924
[45] Date of Patent: Oct. 29, 1996

[54] TRANSFORMABLE DUAL HEAD SPECT CAMERA SYSTEM

[75] Inventor: Steven J. Plummer, Hudson, Ohio

[73] Assignee: Picker International, Inc., Highland Heights, Ohio

[21] Appl. No.: 292,785

[22] Filed: Aug. 18, 1994

[51] Int. Cl.$^6$ ............................ G01T 1/164; G01T 1/166
[52] U.S. Cl. .................................. 250/363.05; 250/363.08
[58] Field of Search ........................ 250/363.05, 363.08; 378/15

[56] References Cited

U.S. PATENT DOCUMENTS

| | | | |
|---|---|---|---|
| 4,204,123 | 5/1980 | Stoddart | 250/363.05 |
| 5,039,859 | 8/1991 | Sanz et al. | 250/363.05 |
| 5,367,169 | 11/1994 | Pierfitte | 250/363.05 |
| 5,444,252 | 8/1995 | Hug et al. | 250/363.05 |

OTHER PUBLICATIONS

Sopha Medical Advertising Brochure, 1993 (2 pp.).
ADAC Laboratories Advertisement, 1993 (3 pp.).

*Primary Examiner*—Davis L. Willis
*Assistant Examiner*—Richard Hanig
*Attorney, Agent, or Firm*—Fay, Sharpe, Beall, Fagan, Minnich & McKee

[57] ABSTRACT

A SPECT camera system has two detector heads (16a, 16b) which are movable between position (FIG. 2) and an adjacent, orthogonal position (FIG. 3). The detector heads have slide members (42a, 42b) which are slidably received on linear guide members (40a, 40b) of carriers (16a, 16b). The carriers have followers (20a, 22a, 24a; 20b, 22b, 24b) which are slidably received along linear guide paths (26a, 28a, 30a; 26b, 28b, 30b). Hydraulic or other extensible cylinders (32a, 32b) selectively permit the carriers, hence the detector heads, to slide along the guide paths between the 180° opposite and the adjacent, orthogonal positions. Preferably, a rotating gantry (12) is rotated to place both detector heads above an intended position. In this manner, the extensible cylinders controllably lower the detector heads as they move by gravity from the present position to the intended position. In both the 180° opposite and the adjacent orthogonal positions, the detector heads concurrently rotate around an axis of rotation (14a) and move radially in and out to minimize the distance between the subject and the detector head.

12 Claims, 3 Drawing Sheets

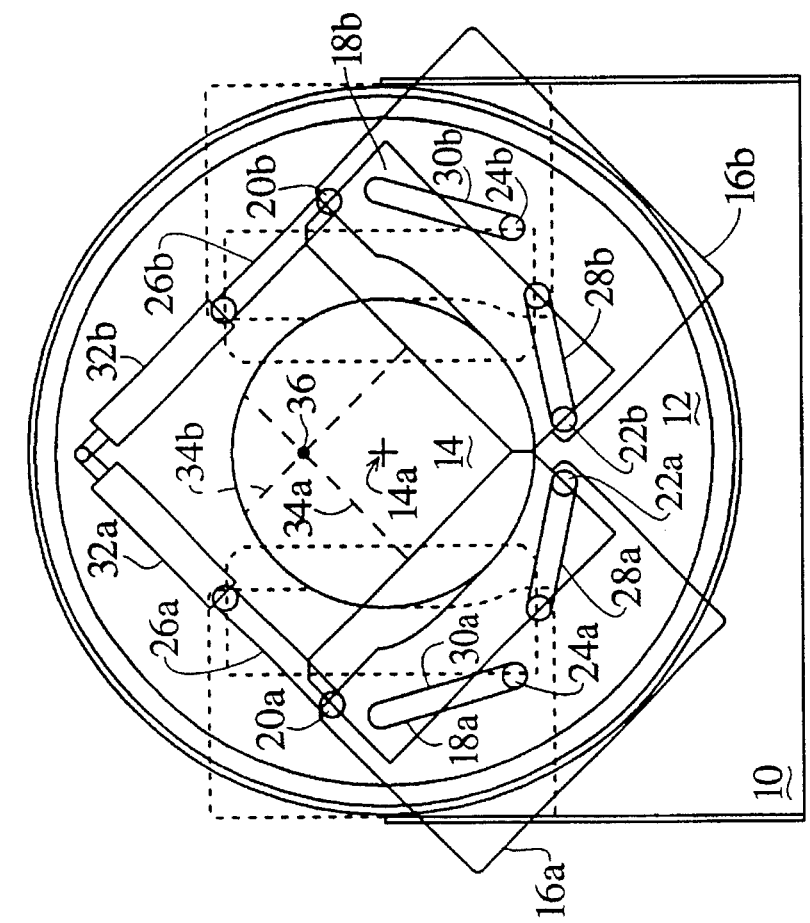
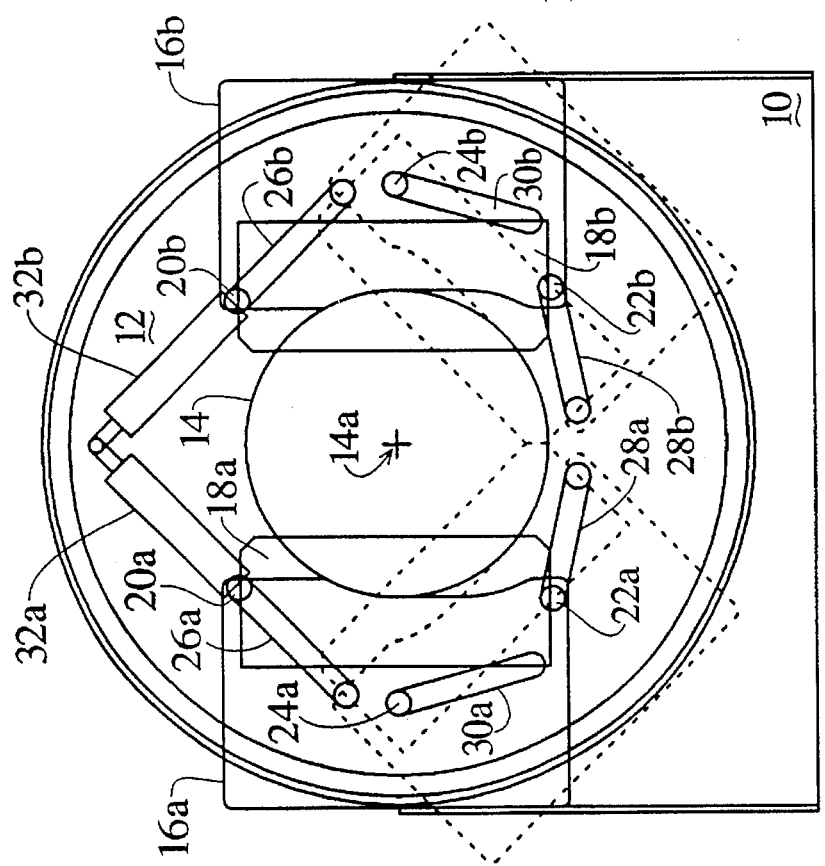
Fig.3
Fig.2

TRANSFORMABLE DUAL HEAD SPECT CAMERA SYSTEM

BACKGROUND OF THE INVENTION

The present invention relates to the nuclear medicine art. It finds particular application in conjunction with two head single photon emission computed tomography (SPECT) camera systems and will be described with particular reference thereto.

Early nuclear or Anger cameras had a single radiation detector head which was positioned stationarily over a region of interest of the subject. The subject was injected with a radioactive dye which circulated through the patient's circulatory system. Some of the radiation given off by the dye was received by the nuclear camera head which converted the radiation event into light.

More specifically, the nuclear camera head included a scintillation plate which converted each radiation event into a scintillation or flash of light. An array of photomultiplier tubes positioned in back of the scintillator plate and associated circuitry determined an (x,y) coordinate location and an energy or (z) value for each scintillation event. A collimator including a grid-like array of lead vanes limited the path or trajectory of radiation events which could strike the scintillation plate. Typically, the collimator constrained each incremental element of the scintillator plate to be receptive only to radiation directly in front of it, i.e., radiation along paths substantially perpendicular to the scintillator plate. In this manner, a shadowgraphic image of the frequency of radiation events in the examined region of the subject was developed.

When the detector head was rotated around the subject or indexed to a multiplicity of angularly offset positions around the subject, a data set was collected which is the mathematical equivalent of a CT scanner data set. More accurately, because the nuclear camera head is two-dimensional, a series of data sets were collected which each corresponded to one slice of an imaged volume.

As with CT scanners, rotating the detector head 180° around the subject produced a complete data set. For faster or more detailed imaging, two detector heads have been mounted to the gantry for rotation around the patient. Typically, the two detector heads have been placed 180° opposite to each other. The 180° opposite orientation has numerous advantages. Mechanically, the detector heads and their lead collimators are very massive. By positioning a pair of detector heads opposite to each other, a counterbalance effect is achieved which simplifies or reduces the strength of mechanical bearings, gears, and actuators needed for rotating the gantry. A second advantage resides in the reconstruction process. When the heads are positioned 180° opposite to each other, both heads view the same rays or paths through the subject. This doubles the data acquisition rate and enables data collected by the two heads to be combined in real time for computational efficiency. Of course, when the heads are positioned 180° opposite to each other, 180° of rotation is still required to generate a complete data set.

Rather than placing the two detector heads 180° apart on the gantry, advantages have been achieved by placing the detector heads 90° apart. When two detector heads are placed 90° apart, a complete data set can be collected in only 90° of rotation. Note that during the first 90° of rotation, each detector head is viewing unique rays. After 90° of rotation, each detector head starts receiving data along rays which the other detector head previously sampled.

Regardless whether the detector heads are placed 180° apart or 90° apart, it is advantageous to position the patient as close as possible to the detector head. Because the human torso is generally not circular, the detector heads are typically movable radially from an axis of rotation such that they can follow the contours of the patient's body.

Heretofore, gantries with 180° opposed detector heads have been adapted to reposition the detector heads 90° apart. However, repositioning the detector heads 90° apart has been a relatively complex mechanical movement. After being positioned in the 90° apart position, the heads are not movable radially about the center of rotation. In one system, the heads are so large that they touch at their corners before reaching a minimal spacing from the patient. In another system, the mechanical arrangement which enables the heads to be shifted between 180° and 90° cannot accommodate radial movement. To maintain the minimal patient/detector head spacing in the 90° detector position, the prior art systems move the patient relative to the detector heads. That is, while the detector heads rotate a fixed radius from the center of rotation, the position of the patient is shifted along vertical and horizontal axes to maintain the patient a minimal distance from the detector heads.

The present invention provides a new and improved SPECT camera system which provides the benefits of both 180° opposite and 90° position detector heads.

SUMMARY OF THE INVENTION

In accordance with the present invention, a two head SPECT camera system is provided in which the detector heads are movable between oppositely disposed positions and adjacent orthogonal positions. In at least the orthogonal position, the heads move radially relative to an axis of rotation as the heads rotate around the axis of rotation.

In accordance with another more limited aspect of the present invention, the heads are supported on carriers for sliding, general radial movement toward and away from an examination region. The carriers are movable between the oppositely disposed and adjacent, orthogonal positions.

In accordance with another more limited aspect of the present invention, a mechanical drive arrangement is provided for moving the heads between the oppositely disposed and adjacent, orthogonal positions. The mechanical drive means includes a pair of linear guide tracks or paths and an actuator for moving the heads along the linear guide paths.

In accordance with another aspect of the present invention, a method of SPECT camera imaging is provided. The heads are moved between oppositely disposed and adjacent, orthogonal orientations. The heads are moved linearly in a generally radial direction toward and away from a subject examination region in both the oppositely disposed and orthogonal orientations as the heads are rotated around the subject.

In accordance with a more limited aspect of the present invention, the heads are mounted on a rotating gantry. The gantry is rotated before repositioning the heads such that gravity assists in moving the heads from their current position to the other of the oppositely disposed and adjacent, orthogonal positions.

One advantage of the present invention is that it achieves the advantages of both 180° opposite positioning of the detector heads and adjacent, orthogonal positioning of the detector heads.

Another advantage of the present invention is that it easily and quickly repositions the detector heads.

Another advantage of the present invention is that it uses gravity to assist the repositioning and enables mechanical components to be lighter-weight and more compact.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 2 is a diagrammatic illustration of the mechanical linkage for moving the detector heads between the 180° opposite position shown in solid lines and the adjacent, orthogonal position shown in phantom;

FIG. 3 is a diagrammatic illustration of the linkage with the detector heads in the adjacent, orthogonal orientation shown in solid line and the 180° opposite orientation shown in phantom; and, FIG. 4 is a side view in partial section of the SPECT camera system of FIG. 3 with the detector heads in the 180° opposite position and oriented at 12 o'clock and 6 o'clock.

DETAILED DESCRIPTION OF THE PREFERRED EMBODIMENT

Figure 1:
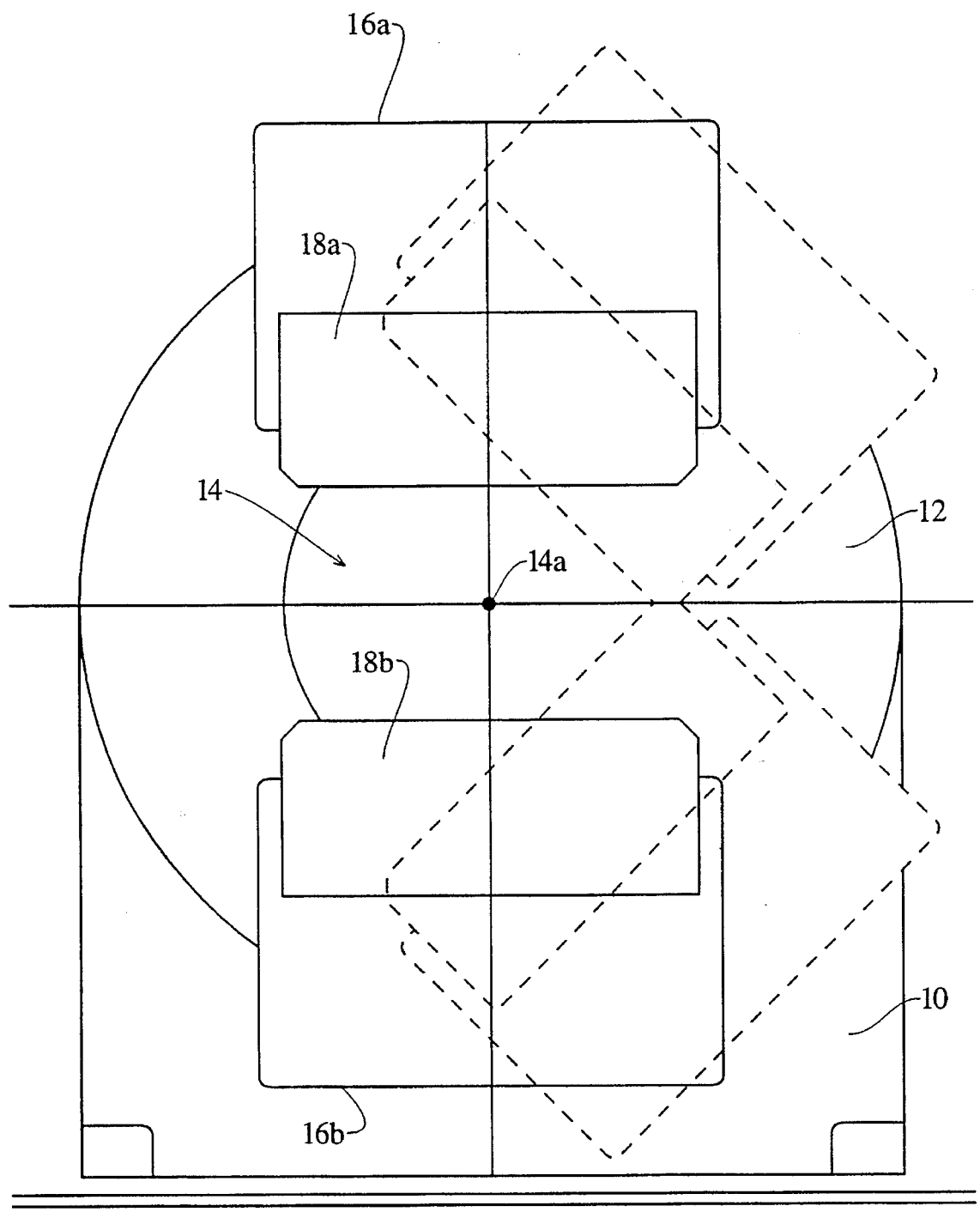
FIG. 1 is a diagrammatic, front view illustration of a SPECT gantry with the detector heads 180° opposite in solid line and in an adjacent, orthogonal position in phantom.

With reference to FIG. 1, a stationary gantry portion 10 supports a rotating gantry 12 for rotation about an axis of rotation 14a at the center of an examination region 14. The rotating gantry carries a pair of detector head carriers 16a, 16b, each of which carry a detector head 18a, 18b, respectively.

Each detector head includes a scintillation plate facing orthogonal to the region of interest 14 and an array of photodetectors for monitoring the scintillation plate for scintillations. A collimator is mounted between the scintillation plate and the examination region. The photodetectors are connected with circuitry for resolving (x,y) coordinates of each scintillation event. An angular position resolver means determines the angular position of the detector heads around the examination region and a radial position resolver determines a radial displacement of each detector head from the center of the examination region. From the (x,y) coordinate positions on the detector heads, the angular orientation and the radial position of the detector heads, a three-dimensional reconstruction means reconstructs a three-dimensional image representation of the subject for display on a video monitor or the like.

To move the detector heads from the 180° opposite orientation (FIG. 2) to the adjacent, orthogonal position (FIG. 3), the detector heads are preferably positioned at 3 o'clock and 9 o'clock. Gravity urges followers 20a, 22a, 24a on the carrier plate 16a to slide along linear guide paths 26a, 28a, 30a, respectively, in the rotating gantry 12. Analogously, followers 20b, 22b, and 24b connected with the carrier a are urged to slide along linear guide paths 26b, 28b, and 30b, respectively. A pair of hydraulic cylinders 32a, 32b are electronically controlled to limit the rate at which the detector head carriers 16a, 16b move between the oppositely disposed and adjacent, orthogonal positions.

The hydraulic cylinders slowly extend, allowing the detector head carriers and detector heads to move under the force of gravity and the urging of the hydraulic cylinders from the 180° opposite of FIG. 2 to the adjacent, orthogonal position of FIG. 3. In the orthogonal position, the heads are off center from the axis of rotation. Planes 34a and 34b that are perpendicular to a central axis of the heads radiation receiving faces intersect along a line 36. The line 36 is further from the radiation receiving faces than the axis of rotation 14a.

To return the detector heads from their adjacent, orthogonal position to the 180° opposite position, the gantry is preferably rotated 180° placing the detector heads adjacent the top of the gantry. The hydraulic cylinders then control the gradual lowering of the detector heads and carriers back to the 180° opposite position of FIG. 2. Alternately, the rotatable gantry can be rotated 90° from the position illustrated in FIG. 2 and one of the heads lowered, and then rotated in the opposite direction and the other head lowered. In the 180° opposition position, the center lines of the detector faces and the axis of rotation are in a common plane.

Figure 4:
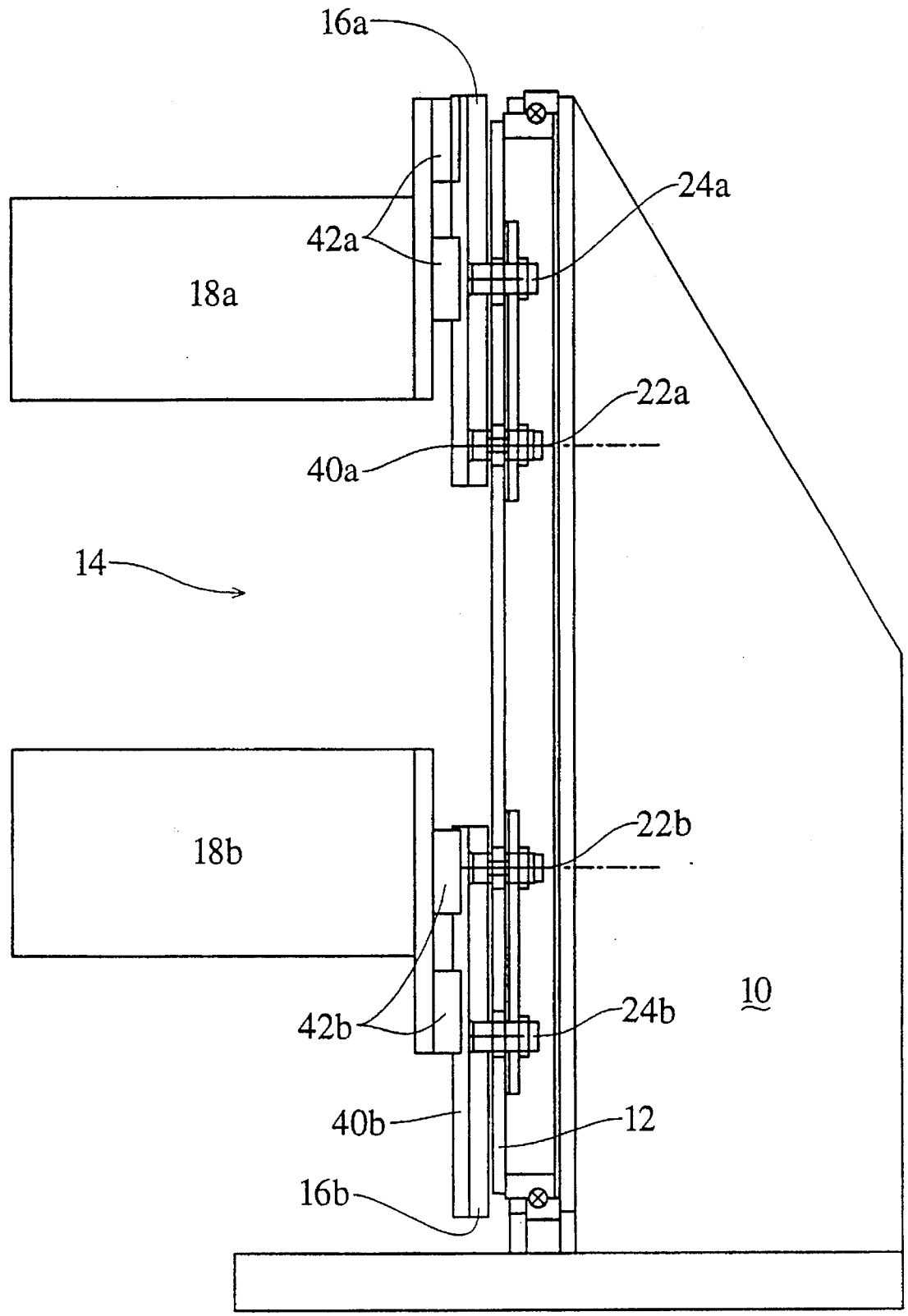

With reference to FIG. 4, each of the carriers include a plurality of linear guide members 40a, 40b which extend substantially parallel to a radial direction from the axis of rotation 14a. Each of the detector heads include a plurality of slide members 42a, 42b which slide along the linear guide members 40. A drive means, such as a worm drive and follower (not shown) selectively adjust the displacement of each detector head radially relative to the axis of rotation. In operation, a subject is positioned with the axis of rotation extending along a central axis of the subject. The detector heads concurrently rotate about the axis of rotation and move radially in and out to minimize a distance between the detector face and the subject.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A SPECT camera system comprising:

a stationary gantry;

a rotating gantry which selectively rotates about an axis of rotation;

a pair of nuclear camera heads supported by the rotating gantry, each camera head having a radiation receiving face;

a repositioning means for moving the two detector heads between (1) a 180° opposite position in which the two nuclear camera heads are disposed on diametrically opposite sides of the axis of rotation and (2) an orthogonal position in which the two detector heads are disposed closely adjacent at adjacent edges with their radiation receiving faces orthogonal to each other and tangentially offset such that rays normal to geometric centers of the radiation receiving faces intersect at an intersection point displaced from the axis of rotation and further from the adjacent edges than the axis of rotation;

a radial movement means for moving the two detector heads along the normal rays in both the 180° opposite position and the orthogonal position to position the detector heads a minimal proximity from the subject as the gantry rotates around the axis of rotation without moving the subject radially relative to the axis of rotation.

2. The SPECT camera system as set forth in claim 1 wherein the repositioning means includes:

guide paths for each detector head, the guide paths being defined along the rotating gantry, and followers for movement along the guide paths mounted for movement with each detector head; and a means for selectively controlling sliding movement of the followers through the guide paths.

3. The SPECT camera system as set forth in claim 2 wherein there are linear guide paths associated with each detector head and a follower for each linear guide path.

4. The SPECT camera system as set forth in claim 1 wherein each of the detector heads is supported by a carrier, and the repositioning means is connected with the carriers for moving both the carriers and the supported detector heads relative to the rotating gantry.

5. The SPECT camera system of claim 4 wherein the radial movement means includes:

linear guide members mounted to each carrier parallel to the normal rays;

slide means on each detector head for sliding movement along the linear guide members; and a means for selectively sliding the detector head and slide means along the linear guide members.

6. The SPECT camera system as set forth in claim 5 wherein the repositioning means includes:

a pair of linear guide paths for each detector head;

a pair of followers for movement along the guide paths mounted for movement with each detector head; and a means for selectively controlling sliding movement of the followers along the linear guide paths.

7. A method of positioning detector heads of a dual head SPECT camera which includes a stationary gantry on which a rotary gantry is rotatably mounted for rotation about an axis of rotation and a pair of detector heads each with a radiation receiving face movably supported on the rotating gantry, the method comprising:

selectively moving the camera heads between (1) a 180° opposite position in which the detector heads are disposed diametrically opposite across a subject and facing each other with a central axis of each detector head radiation receiving face and the axis of rotation being co-planar and (2) a tangentially-offset, orthogonal position in which the two detector heads are disposed closely adjacent and face the subject in directions orthogonal to each other, in the tangentially-offset, orthogonal position, planes which are orthogonal to the radiation receiving faces of the two detector heads and intersect their central axis lie parallel to the axis of rotation and intersect each other further from the detector head faces than the axis of rotation, whereby the central axes of the heads are tangentially offset relative to the axis of rotation;

concurrently rotating the detector heads around the axis of rotation in the tangentially-offset, orthogonal position and moving the detector heads radially relative to the axis of rotation.

8. The method as set forth in claim 7 wherein the moving step further includes:

with the detector heads in the 180° opposite position, positioning the detector heads at substantially 3 o'clock and 9 o'clock;

controllably permitting gravity to lower the detector heads from the 180° opposite position to the tangentially-offset, orthogonal position.

9. The method as set forth in claim 8 further including rotating the rotating gantry such that the detector heads in the tangentially-offset, orthogonal position are substantially at an uppermost position;

controllably allowing gravity to lower the detector heads from the tangentially-offset orthogonal position to the 180° opposite position.

10. The method as set forth in claim 7 wherein the detector heads are movably mounted on carriers, the step of moving the detector heads between the 18° and the tangentially-offset, orthogonal positions includes moving the carriers relative to the rotating gantry portion.

11. A SPECT camera system comprising:

a stationary gantry;

a rotating gantry which selectively rotates about an axis of rotation;

a pair of detector head carriers supported by the rotating gantry;

guide paths defined along the rotating gantry and followers for movement along the guide paths mounted with the carriers, the guide paths and followers being configured to permit movement of the carriers between (1) a 180° opposite position and (2) an adjacent orthogonal position, the guide paths and followers being disposed such that a central axis of the detector heads are disposed in a common plane with the axis of rotation in the 180° opposite position and such that planes perpendicular to the central axis of the detector heads are tangentially displaced from the axes of rotation to intersect further from the detector heads than the axis of rotation in the adjacent, orthogonal position;

a mechanical actuator for selectively controlling sliding movement of the followers through the guide paths;

a detector head mounted to each carrier by linear guides and a mechanical drive for providing motive force for moving the detector heads in and out along the linear guides;

such that the detector heads are movable in and out along the common plane in the 180° opposite position and along the planes perpendicular to the central axis that are tangentially displaced from the axis of rotation in the adjacent, orthogonal position.

12. The method as set forth in claim 7 further including:

positioning a subject along the axis of rotation and holding the patient stationary as the detector heads are rotated around the axis of rotation with the detector heads in the tangentially-offset, orthogonal position, such that the detector heads are disposed closely adjacent the subject.

* * * * *